United States Patent [19]

Bertleff et al.

[11] Patent Number: 4,861,895

[45] Date of Patent: Aug. 29, 1989

[54] TREATMENT OF AQUEOUS SOLUTIONS OBTAINED IN THE CARBALKOXYLATION OF OLEFINICALLY UNSATURATED COMPOUNDS

[75] Inventors: Werner Bertleff, Viernheim; Robert Maerkl, Fussgoenheim; Peter Magnussen, Bad Duerkheim; Gebhard Kuehn, Ludwigshafen; Peter Stops, Altrip, all of Fed. Rep. of Germany

[73] Assignee: BASF Aktiengesellschaft, Ludwigshafen, Fed. Rep. of Germany

[21] Appl. No.: 77,630

[22] Filed: Jul. 24, 1987

[30] Foreign Application Priority Data

Aug. 21, 1986 [DE] Fed. Rep. of Germany ....... 3628357

[51] Int. Cl.$^4$ .................... C07D 211/70; C07C 67/00; C07C 69/34
[52] U.S. Cl. .................................. 546/353; 560/204; 560/193
[58] Field of Search ................. 560/204, 193; 546/353

[56] References Cited

U.S. PATENT DOCUMENTS 4,258,203 3/1981 Platz et al. ......................... 560/204
4,485,255 11/1984 Jenck ................................. 560/193

OTHER PUBLICATIONS

Patent Abstracts of Japan (1981) 5(12): 119 c 40. Abst. No.: 55-141440.

*Primary Examiner*—John M. Ford
*Assistant Examiner*—Robert C. Whittenbaugh
*Attorney, Agent, or Firm*—Keil & Weinkauf

[57] ABSTRACT

Aqueous solutions which are obtained in the carbalkoxylation of olefinically unsaturated compounds and contain heterocyclic aromatic nitrogen bases, their transformation products and lower fatty acids and/or their salts are treated by a process in which (a) the aqueous solution is heated to 150°–300° C. under from 10 to 300 bar and (b) heterocyclic aromatic nitrogen bases which are formed again from the transformation products are then separated off.

7 Claims, No Drawings

TREATMENT OF AQUEOUS SOLUTIONS OBTAINED IN THE CARBALKOXYLATION OF OLEFINICALLY UNSATURATED COMPOUNDS

The present invention relates to a process for the treatment of aqueous solutions which are obtained in the carbalkoxylation of olefinically unsaturated compounds and contain heterocyclic aromatic nitrogen bases, their transformation products and lower fatty acids and/or their salts.

The carbalkoxylation of olefinically unsaturated compounds in the presence of heterocyclic aromatic nitrogen bases gives aqueous solutions which contain such heterocyclic aromatic nitrogen bases and their transformation products and require treatment. European Patent Application No. 0,008,412 discloses a process in which aqueous solutions which contain heterocyclic aromatic nitrogen bases and their transformation products, which are obtained in the preparation of the catalyst, are treated at from 250° to 300° C. This process has the disadvantage that substantial amounts of transformation products of heterocyclic aromatic nitrogen bases still remain in the aqueous solution and, where cobalt salts are present in the aqueous solution, metallic cobalt is also precipitated.

It is an object of the present invention to provide a process for the treatment of aqueous solutions which contain heterocyclic aromatic tertiary nitrogen bases and their transformation products, in which the recovery of the said nitrogen bases is increased and furthermore, where cobalt salts are present, precipitation of metallic cobalt is avoided.

We have found that this object is achieved by a process for the treatment of aqueous solutions which are obtained in the carbalkoxylation of olefinically unsaturated compounds and contain heterocyclic aromatic nitrogen bases, their transformation products and lower fatty acids and/or their salts, wherein (a) the aqueous solution is heated to 150°–300° C. under from 10 to 300 bar and (b) the tertiary aromatic nitrogen bases which are formed again from the transformation products are then separated off.

One advantage of the novel process may be that heterocyclic aromatic nitrogen compounds present are separated off before the treatment under pressure and at elevated temperatures.

The novel process has the advantages that it is simple to carry out and is not technically complicated, and the yield of heterocyclic aromatic nitrogen bases which are recovered is increased. Another advantage of the novel process is that precipitation of metallic cobalt is avoided where cobalt salts are present in the aqueous solution. Where this is the case, the advantage of the novel process is that these solutions can readily be used for the preparation of catalysts for the carbalkoxylation without undesirable precipitation taking place in the course of the process.

According to the invention, aqueous solutions which contain heterocyclic aromatic tertiary nitrogen bases, their transformation products and lower fatty acids and/or their salts are used as starting materials. Preferred heterocyclic aromatic nitrogen bases are pyridine, quinoline or isoquinoline, each of whixh may be substituted by one or two alkyl radicals of 1 to 10 carbon atoms, cycloalkyl radicals of 5 to 8 carbon atoms, aralkyl radicals of 7 or 8 carbon atoms or aryl radicals of 6 to 10 carbon atoms, for example phenyl radicals. Preferred substituents are alkyl radicals having the stated number of carbon atoms. In particular, the aqueous solutions contain pyridine or alkyl- or dialkylpyridines where alkyl is of 1 to 4 carbon atoms. A rule, such heterocyclic aromatic nitrogen bases are present in the aqueous solution in an amount of from 1 to 10% by weight.

For the purposes of the present invention, transformation products of heterocyclic aromatic nitrogen bases are the compounds formed from such nitrogen bases during the carbalkoxylation. These include a large number of nitrogen compounds whose composition is not known in detail. Where pyridine is used as the nitrogen compound, the products formed are, for example, N-methylpyridinium salts, N-methyldihydropyridine and higher molecular weight nitrogen bases and other amines. Such transformation products of heterocyclic aromatic nitrogen bases are present in the aqueous solution in general in an amount of from 1 to 10% by weight.

Preferred lower fatty acids are of 1 to 4, in particular 2 or 3, carbon atoms. Examples of suitable fatty acids are acetic acid, propionic acid and butyric acid. As a rule, the aqueous solution contains acetic acid. The fatty acids are present in general in a concentration of 3 to 20% by weight.

Preferred salts of lower fatty acids are alkali metal salts, in particular potassium or sodium salts. As a rule, the salts are potassium or sodium salts of the abovementioned fatty acids, in particular acetates. Such salts are present in general in an amount from 5 to 25% by weight.

The aqueous solutions may furthermore contain cobalt salts of the abovementioned lower fatty acids, in particular cobalt acetate. In general, the content of cobalt salts is from 0.1 to 10% by weight.

A typical starting solution contains, for example, from 3 to 6% by weight of heterocyclic aromatic tertiary nitrogen bases, from 1 to 8% by weight of their transformation products, from 5 to 10% by weight of acetic acid and from 3 to 8% by weight of cobalt acetate. Another typical starting solution contains, for example, from 0.1 to 1% by weight of heterocyclic aromatic tertiary nitrogen bases, from 3 to 10% by weight of their transformation products and from 10 to 15% by weight of sodium acetate. Such solutions are obtained, for example, in the oxidative removal of cobalt after carbalkoxylation, after the extraction of the cobalt carbonyl catalyst, where cobalt salt solutions from the oxidative removal of cobalt are recycled for the preparation of the catalyst, or cobalt is precipitated from such solutions, for example with sodium carbonate, and separated off.

Advantageously, the free heterocyclic aromatic tertiary nitrogen bases are first separated off from the aqueous solutions requiring treatment. This is done, for example, by stripping with the inert gases or with steam, in particular by distillation as an azeotrope with water.

However, this separation is not essential since the presence of heterocyclic aromatic nitrogen bases in small concentrations of about 1–5% by weight does not affect the subsequent steps.

The remaining aqueous solution is then heated to 150°–300° C., in particular 150°–240° C., preferably 160°–240° C., under from 10 to 300, in particular from 10 to 50, bar, advantageously under the resulting autogenous pressure. The time of treatment is, as a rule, from 15 to 240 minutes.

It has proven useful to carry out the treatment in the presence of an oxidizing agent. Examples of suitable oxidizing agents are hydrogen peroxide, molecular oxygen and gases containing molecular oxygen, e.g. air. The presence of an oxidizing agent has proven particularly useful in the treatment of aqueous solutions containing cobalt salts.

After the thermal treatment, the heterocyclic aromatic tertiary nitrogen bases now formed again from the transformation products are separated off, for example by stripping with inert gases or steam, in particular by distillation as an azeotrope with water. The azeotropes of heterocyclic aromatic tertiary nitrogen bases with water are advantageously worked up together and, for example, water is removed by distillation with entraining agents and pure nitrogen bases are obtained.

The Examples which follow illustrate the process according to the invention.

EXAMPLE 1

3 moles of methyl 3-pentenoate, 0.6 mole of the nitrogen bases stated below, 3.75 moles of methanol and 0.13 mole of cobalt as cobalt octacarbonyl were initially taken in a high pressure vessel. The reaction was carried out using carbon monoxide at 165° C. and under 280 bar for 20 hours. After the mixture had been cooled and let down, 300 ml of water and 50 g of acetic acid were added to the discharged mixture, which was then refluxed for 1 hour while air was passed in. The mixture was cooled and then extracted with 300 ml of cyclohexane. The remaining part of the nitrogen base used was completely distilled off from the resulting aqueous phase, as an azeotrope with water. The remaining bottom product was heated at 250° C. for 4 hours under autogenous pressure in a high pressure vessel. The mixture was cooled and let down, after which the nitrogen base formed again was distilled off and determined. The results for the individual nitrogen bases are shown in the Table below.

TABLE 1

| N base | % loss after carbalkoxylation | Re-formation in g after thermal treatment | % recovery |
|---|---|---|---|
| pyridine | 24.4 | 6.14 | 52.4 |
| beta-picoline | 27.8 | 6.25 | 40.3 |
| gamma-picoline | 28.5 | 4.77 | 30.0 |

EXAMPLE 2

The procedure described in Example 1 was followed, but beta-picoline was used as the nitrogen base and the thermal treatment was carried out at various temperatures. The temperatures and the results obtained are shown in the Table below.

| Temperature | Content of beta-picoline in % after thermal treatment | % recovery | Co loss in % |
|---|---|---|---|
| (a) 185° C. | 0.63 | 10.9 | 0 |
| (b) 200° C. | 1.20 | 23.6 | 0 |
| (c) 250° C. | 2.61 | 51.5 | 0 |
| (d) 300° C. | 2.80 | 55.3 | 30 |

EXAMPLE 3

The procedure described in Example 1 was followed, beta-picoline being used as the nitrogen base and the thermal treatment being carried out at 300° C., except that the high pressure vessel was subjected in the cold state to air under 10 bar. The resulting discharged mixture contained 3.7% by weight of picoline. The recovery rate was 73.1%. Cobalt was not precipitated.

EXAMPLE 4

The procedure described in Example 1 was followed, except that the aqueous phase containing 2.56% by weight of beta-picoline and originating from the oxidative removal of cobalt was used directly for the thermal treatment, which was carried out at 250° C. The resulting aqueous solution contained 3.4% by weight of beta-picoline, corresponding to a recovery of 20.7%. Cobalt was not precipitated.

EXAMPLE 5

The procedure described in Example 1 was followed, 20.4% of the beta-picoline being converted. The remaining beta-picoline was completely separated, by azeotropic distillation, from the aqueous phase obtained in the oxidative removal of cobalt, and the remaining aqueous solution was reacted with $CO/H_2$ in a molar ratio of 1:1 at 150° C. and under 280 bar. The cobalt carboxyl hydride formed was extracted with pentane, and the remaining aqueous phase was treated for 4 hours at 250° C. under autogenous pressure. The material discharged contained 225% of betapicoline, corresponding to a recovery of 59.1%.

EXAMPLE 6

The procedure described in Example 1 was followed (19.6% beta-picoline converted), free beta-picoline was completely separated off by azeotropic distillation from the aqueous phase obtained in the oxidative removal of cobalt, and the cobalt present was precipitated from the remaining aqueous solution after neutralization with NaOH, by a 10-fold molar excess of $Na_2CO_3$, in the form of sparingly soluble $C° C.O_3$. The mother liquor was treated for 4 hours at 250° C. under autogenous pressure. The material discharged contained 1.88% of beta-picoline, corresponding to a recovery of 51.5%.

We claim:

1. A process for the treatment of an aqueous solution which is obtained in the carbalkoxylation of olefinically unsaturated compounds and contains heterocyclic aromatic tertiary nitrogen bases, their transformation products and lower fatty acids and/or their salts, which comprises:
    (a) heating the aqueous solution to 150°–300° C. under from 10 to 300 bar, and
    (b) separating off the heterocyclic aromatic nitrogen bases which are formed again from the transformation products by distillation.

2. The process of claim 1, wherein free heterocyclic aromatic tertiary nitrogen bases are first separated off from the aqueous solution.

3. The process of claim 1, wherein the starting solution used contains cobalt salts of lower fatty acids.

4. The process of claim 1, wherein the thermal treatment in stage a is carried out in the presence of molecular oxygen or a gas containing molecular oxygen.

5. The process of claim 1, wherein the thermal treatment is carried out at from 150° to 240° C.

6. The process of claim 1, wherein the heterocyclic aromatic nitrogen bases are separated off by distillation as azeotropes with water.

7. The process of claim 1, wherein the heterocyclic aromatic nitrogen bases are separated by stripping with an inert gas or steam.

* * * * *